(12) United States Patent
Williams et al.

(10) Patent No.: US 7,300,638 B2
(45) Date of Patent: Nov. 27, 2007

(54) STERILIZATION DEVICE FOR STERILIZATION OF LUMEN DEVICES

(75) Inventors: Kevin O. Williams, Solon, OH (US); Christopher J. Justi, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 584 days.

(21) Appl. No.: 10/848,184

(22) Filed: May 18, 2004

(65) Prior Publication Data

US 2005/0260097 A1    Nov. 24, 2005

(51) Int. Cl.
*A61L 2/20* (2006.01)
(52) U.S. Cl. .................... 422/292; 422/300
(58) Field of Classification Search ............. None
See application file for complete search history.

(56) References Cited

U.S. PATENT DOCUMENTS

| | | | |
|---|---|---|---|
| 4,410,492 A | * | 10/1983 | Kaye ........................ 422/27 |
| 4,943,414 A | | 7/1990 | Jacobs et al. ............... 422/28 |
| 5,348,711 A | * | 9/1994 | Johnson et al. ............ 422/300 |
| 6,162,395 A | | 12/2000 | Kowanko .................... 422/33 |
| 6,365,103 B1 | | 4/2002 | Fournier ..................... 422/33 |
| 6,451,255 B1 | | 9/2002 | Williams et al. ............. 422/33 |
| 2001/0036422 A1 | | 11/2001 | Lin et al. .................... 422/28 |

* cited by examiner

*Primary Examiner*—E. Leigh McKane
(74) *Attorney, Agent, or Firm*—Kusner & Jaffe; Michael A. Centanni

(57) ABSTRACT

An apparatus for the sterilization of lumen devices. The apparatus for sterilizing lumen devices is comprised of a chamber defining a region for sterilization, an expansion tank assembly, and a mixing member. The chamber is adapted to receive the expansion tank. The expansion tank is adapted to fluidly connect to at least one lumen device. The mixing member is disposed within the expansion tank to mix gaseous sterilant within residual gas that may include contaminants.

12 Claims, 2 Drawing Sheets

STERILIZATION DEVICE FOR STERILIZATION OF LUMEN DEVICES

FIELD OF THE INVENTION

The present invention relates to sterilizers and the like, and more particularly to a sterilization device for sterilizing lumen devices with a gaseous chemical.

BACKGROUND OF THE INVENTION

Various systems and apparatus have been developed to sterilize lumen devices, such as endoscopes and other devices having a lumen. Methods of sterilizing lumen devices may utilize a sterilization chamber and one or more gaseous sterilants, such as ozone or vaporized hydrogen peroxide (VHP). In order to achieve effective sterilization, all contaminants within the lumen device must be exposed to the gaseous sterilant, including contaminants suspended in the air within the lumen device and contaminants on interior and exterior surfaces of the lumen device. However, the length of a lumen is many times greater than its diameter and such geometry can make it difficult to penetrate the lumen (i.e., interior passageway) with a gaseous sterilant.

Known methods for sterilizing a lumen cause a gaseous sterilant to flow through the lumen by creating a difference in pressure across the length of the lumen (i.e., pressure drop). Existing apparatus and methods used to create adequate pressure drop across the length of a lumen have various drawbacks. Such drawbacks include complexity, limitations on the types of devices that can be sterilized, and possible recontamination of the lumen when the gaseous sterilant is withdrawn from the lumen.

One prior art method for creating a pressure drop to sterilize lumen devices utilizes an expansion tank disposed within a sterilization chamber. A first end of a lumen is fluidly connected to the expansion tank, and a second end of the lumen is open to the sterilization chamber. In this respect, the lumen fluidly connects the expansion tank with the sterilization chamber. The volume of the expansion tank is such that all of the unsterile air contained within the lumen can be forced into the expansion tank during the sterilization cycle. The purpose of the expansion tank is to provide a chamber that will be at a lower pressure than the sterilization chamber, and thus "draw" gaseous sterilant through the lumen.

An expansion tank is used in a sterilization process in the following manner. First, a vacuum is drawn on the sterilization chamber, and the pressures within the sterilization chamber and the expansion tank are allowed to equalize. Next, a gaseous sterilant is introduced into the sterilization chamber. Thereafter, the pressure of the sterilization chamber is allowed to rise above the pressure in the expansion tank. The resulting difference in pressures between the sterilization chamber and the expansion tank causes the gaseous sterilant to flow through the lumen and into the expansion tank. The gaseous sterilant will continue to flow into the expansion tank until the pressure in the sterilization chamber and the pressure in the expansion tank have equalized, and the concentration of the sterilant is at a desired level. After a suitable period, a vacuum is again drawn on the sterilization chamber, thereby removing the gaseous sterilant from the sterilization chamber. As the pressure decreases within the sterilization chamber, the gaseous sterilant is drawn out of the expansion tank through the lumen and into the sterilization chamber. After the pressure drops to a desired level, a second gas (e.g., air) is introduced into the sterilization chamber to purge the remaining gaseous sterilant using an analogous series of steps.

Various problems may be encountered when using prior art expansion tanks to sterilize lumen devices. One problem is inadequate sterilization caused by the presence of unsterile air within the expansion tank and the lumen. In this regard, some unsterile air may remain within the lumen after a vacuum has been drawn on the sterilization chamber. When a gaseous sterilant is introduced into the lumen, the remaining unsterile air may be pushed ahead of the gaseous sterilant through the lumen and into the expansion tank. The unsterile air poses a problem because it does not actively mix with the gaseous sterilant, due to nonturbulent flow (i.e., plug flow). It is possible for the sterilant to penetrate unsterile air without active mixing by gas diffusion. However, gas diffusion is a slow process, and does not insure that all contaminates are adequately exposed to the gaseous sterilant. Accordingly, the unsterile air can contain viable organisms that survive the sterilization process. The surviving viable organisms may be subsequently drawn back into the lumen as gas is withdrawn from the sterilization chamber. The surviving viable organisms can then compromise sterility of the lumen device by re-depositing in the lumen.

The present invention overcomes the above-mentioned drawbacks and others associated with prior art systems for sterilization of lumen devices.

SUMMARY OF THE INVENTION

In accordance with the present invention, there is provided an apparatus for the sterilization of lumen devices comprising: (a) an expansion tank assembly fluidly connectable with at least one lumen device; (b) a housing defining a sterilization chamber being dimensioned to receive said expansion tank assembly; and (c) at least one mixing member disposed within said expansion tank assembly.

In accordance with another aspect of the present invention, there is provided a method for the sterilization of lumen devices in a sterilization apparatus comprising a sterilization chamber and an expansion tank assembly disposed therein, the method including the steps of: (a) introducing a gaseous sterilant into the sterilization chamber and the expansion tank assembly; and (b) mixing the gaseous sterilant with any residual gas inside said expansion chamber using a mixing member to form a mixed gas.

An advantage of the present invention is the provision of an apparatus for sterilizing a lumen device by drawing a gaseous sterilant through a lumen.

A still further advantage of the present invention is the provision of an apparatus that generates a turbulent flow to mix gaseous sterilant with unsterile air.

A still further advantage of the present invention is the provision of an apparatus for sterilizing a lumen device that exposes unsterile air within an expansion tank to a gaseous sterilant.

A still further advantage of the present invention is the provision of an apparatus for sterilizing a lumen device that exposes unsterile air within a lumen to a gaseous sterilant.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
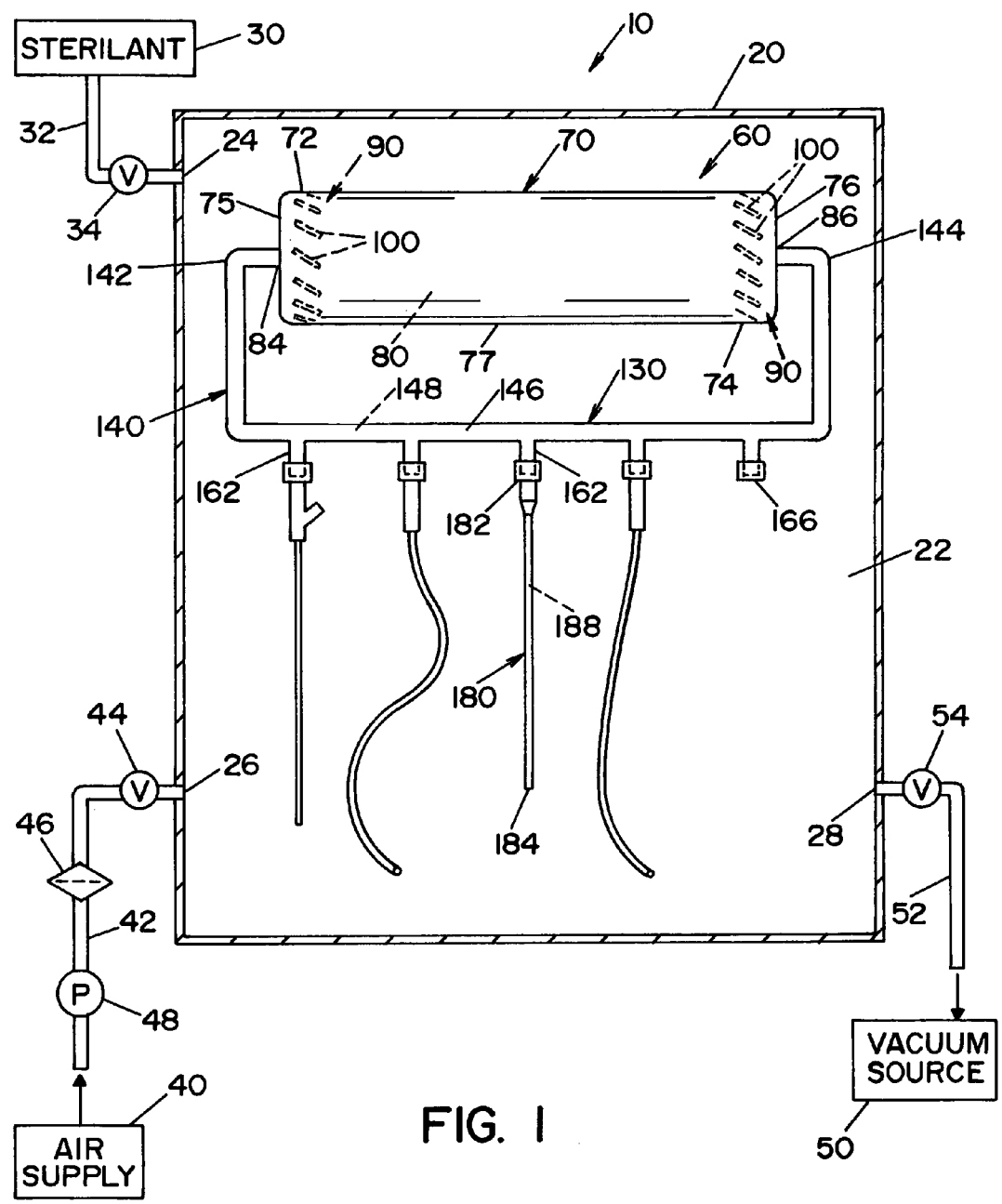
FIG. 1 is a schematic cross-sectional view of a sterilization apparatus for lumen devices, including an expansion tank assembly according to a preferred embodiment of the present invention.

Referring now to the drawings wherein the showings are for the purposes of illustrating a preferred embodiment of the invention only and not for purposes of limiting same, FIG. 1 shows a sterilization apparatus 10 illustrating a preferred embodiment of the present invention. In the embodiment shown, sterilization apparatus 10 is generally comprised of a housing 20, an expansion tank assembly 60, and at least one mixing member 90.

Housing 20 defines a treatment chamber 22. In the illustrated embodiment, housing 20 has a first input port 24, a second input port 26, and an output port 28. A first conduit 32 fluidly connects first input port 24 of housing 20 with a sterilant supply 30. In a preferred embodiment, sterilant supply 30 provides a source of at least one gaseous/vaporous sterilant (hereinafter, gaseous sterilant) including, but not limited to, vaporized hydrogen peroxide (VHP), ozone, ethylene dioxide, and chlorine dioxide. A first valve 34 is disposed along first conduit 32 to control the flow of gaseous sterilant into treatment chamber 22.

A second conduit 42 fluidly connects an air supply 40 with second input port 26 of housing 20. Air supply 40 provides a source of sterile air. A pump 48 is provided along second conduit 42 to convey sterile air from air supply 40 through second conduit 42. A second valve 44 and a filter 46 are disposed along second conduit 42. Second valve 44 controls the flow of sterile air into treatment chamber 22.

Output port 28 of housing 20 is fluidly connected with a vacuum source 50 via a third conduit 52. A third valve 54 is disposed along conduit 52. Third valve 54 controls whether a vacuum is drawn.

Figure 2:
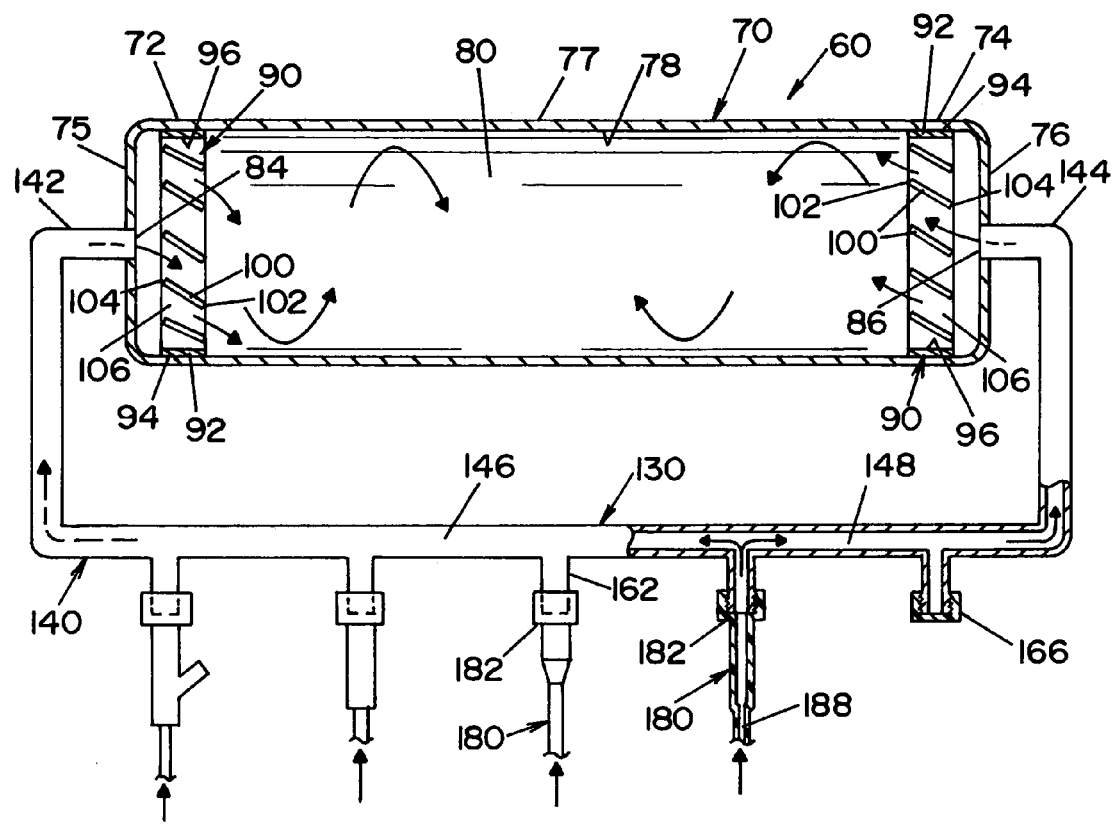
FIG. 2 is a partially sectioned plan view of an expansion tank assembly comprised of an expansion tank and manifold as shown in FIG. 1.

As can best be seen in FIG. 2, expansion tank assembly 60 includes an expansion tank 70 and a manifold 130. In the embodiment shown, expansion tank 70 has a first end wall 75, a second end wall 76, and a generally cylindrical wall 77. Cylindrical wall 77 has a curved inner surface 78. In the embodiment shown, first end wall 75, second end wall 76, and cylindrical wall 77 define an inner chamber 80 of expansion tank 70. First end wall 75 has a first port 84 formed therein. Second end wall 76 has a second port 86 formed therein. It is appreciated that expansion tank 70 may have alternate geometries as further described below.

Manifold 130 of expansion tank assembly 60 is generally comprised of a conduit 140 having a first end 142, a second end 144, and a header portion 146. Conduit 140 defines a passageway 148 between first end 142 and second end 144. First end 142 is fluidly connected with chamber 80 of expansion tank 70 via first port 84. Second end 144 is fluidly connected with chamber 80 of expansion tank 70 via second port 86.

In a preferred embodiment, header portion 146 is disposed between first end 142 of conduit 140 and second end 144 of conduit 140. Header portion 146 includes at least one port 162 for fluidly connecting a lumen device with conduit 140. In the illustrated embodiment, port 162 includes a threaded portion dimensioned to threadingly receive a mating portion of a lumen device 180, as best seen in FIG. 2. An unused port 162 may threadingly receive a threaded cap 166.

With reference to FIG. 1, lumen device 180 has a mating end 182 and an open end 184. Mating end 182 is adapted to threadingly connect to port 162 of header portion 146. Lumen device 180 defines a passageway 188 between mating end 182 and open end 184. Open end 184 of lumen device 180 defines an opening that fluidly connects chamber 80 with treatment chamber 22 by way of passageway 148 of conduit 140, and passageway 188 of lumen device 180.

It should be appreciated that manifold 130 may alternatively be configured to connect with only a single lumen device. Furthermore, manifold 130 may be alternatively configured to connect with expansion tank 70 through only one port of expansion tank 70. In this regard, only first end 142 of conduit 140 or only second end 144 of conduit 140 is connected with expansion tank 80.

Figure 3:
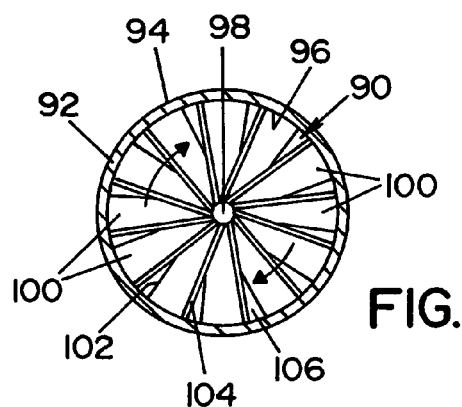
FIG. 3 is a detached end view of a mixing member as shown in FIGS. 1 and 2.

In a preferred embodiment, one or more mixing members 90 are disposed within expansion tank 70, as best seen in FIG. 2. Referring now to FIG. 3, mixing member 90 is comprised of an annular wall 92, a center post 98, and a plurality of vanes 100. Annular wall 92 has an outer surface 94 and an inner surface 96. Center post 98 is generally coaxial with annular wall 92. Vanes 100 are uniformly radially disposed about center post 98, and extend between center post 98 and inner surface 96 of annular wall 92. Vanes 100 are circumferentially attached to annular wall 92. Each of the plurality of vanes 100 has an edge 102 and an edge 104. Vanes 100 define a plurality of regularly disposed slots 106

Referring now to FIG. 2, in the illustrated embodiment, a pair of mixing members 90 are respectively located proximate to first end wall 75 at a first end 72 of expansion tank 70, and to second end wall 76 at a second end 74 of expansion tank 70. In the illustrated embodiment, each mixing member 90 is substantially identical.

In the embodiment shown, mixing member 90 at first end 72 of expansion tank 70 is disposed across the diameter of inner chamber 80. Outer surface 94 of mixing member 90 at first end 72 is generally concentric with and abuts the curved inner surface 78 of expansion tank 70, and is oriented such that edge 104 is proximate to first port 84. Mixing member 90 at second end 74 is disposed across the diameter of inner chamber 80. Outer surface 94 of mixing member 90 at second end 74 is generally concentric with and abuts the curved inner surface 78 of expansion tank 70, and is oriented such that edge 104 is proximate to second port 86.

It should be appreciated that the orientation of mixing members 90 relative to ports 84 and 86 as shown in FIGS. 1 and 2 illustrates a preferred embodiment of the present invention, and it is contemplated that the orientation of one or both mixing members 90 may be modified.

It should also be appreciated that mixing member 90 as illustrated herein is shown solely for illustrating a preferred embodiment of the present invention, and not for limiting same. In this regard, mixing member 90 may have an alternative configuration for producing turbulent flow. Some alternate configurations are discussed below. Furthermore, it should be understood that one or more mixing members 90 may be used to produce turbulent flow. In addition, a combination of mixing members 90 having different configurations may be used together to produce turbulent flow.

Turning now to the operation of sterilization apparatus 10 in a preferred embodiment, a sterilization process can be generally summarized by the following steps: (A) initial setup, wherein one or more lumen devices 180 are attached to expansion tank 70 and placed within treatment chamber 22, (B) initial evacuation, wherein vacuum source 50 is activated to withdraw gas from treatment chamber 22, at least one lumen device 180, and chamber 80 of expansion tank 70; (C) sterilization, wherein a gaseous sterilant from sterilant supply 30 is introduced into treatment chamber 22, one or more lumen devices 180, and expansion tank 70; (D) final evacuation, wherein vacuum source 50 is activated to withdraw gas from treatment chamber 22, one or more lumen devices 180, and chamber 80 of expansion tank 70, and (E) purging, wherein sterile air from air supply 40 replaces gas removed from treatment chamber 22, one or more lumen devices 180, and chamber 80, and brings the pressure within treatment chamber 22, the one or more lumen devices 180 and chamber 80 of expansion tank 70, to match the surroundings or some other suitable level.

It should be understood that references herein to "gas" flowing through components of system 10 may include active gaseous sterilant from sterilant supply 30, sterile air from air supply 40, residual gases (e.g., unsterile air), and combinations thereof. "Residual gases" include unsterile air that remains within the components of system 10 prior to the introduction of a gaseous sterilant into system 10.

The sterilization process described above is provided to illustrate a preferred embodiment of the present invention only and is not intended to limit the scope of the present invention. In this regard, it is contemplated that one skilled in the art would readily recognize variations of the sterilization processing steps including, but not limited to, omitting initial evacuation and simply adding gaseous sterilant to treatment chamber 22, thereby causing the pressure of treatment chamber 22 to rise above the pressure of chamber 80. Consequently, gaseous sterilant will flow into chamber 80.

Operation of the present invention will now be described in detail according to a preferred embodiment. With regard to "initial setup," at least one lumen device 180 is attached to a respective port 162 of manifold 130, thereby putting the lumen device in fluid communication with chamber 80 of expansion tank 70. All unused ports 162 are covered with a threaded cap 166 to provide an "air-tight" seal. Expansion tank 70 and at least one lumen device 180 are disposed within treatment chamber 22.

Turning now to "initial evacuation," third valve 54 is opened to vacuum source 50, thereby withdrawing gas contained within treatment chamber 22, the at least one lumen device 180, and chamber 80. Accordingly, the pressure within treatment chamber 22 is reduced. When the pressure within treatment chamber 22 is at a first pressure (preferably about 1 torr, though it is recognized that pressures other than 1 torr but less than atmospheric are acceptable), third valve 54 is closed. Following that, the pressure within treatment chamber 22 is allowed to equalize with the pressure within chamber 80 of expansion tank 70. It should be appreciated that after initial evacuation some residual gas (e.g., unsterile air) may remain within treatment chamber 22, the at least one lumen device 180, and chamber 80.

"Sterilization" and "final evacuation" will now be described in detail. With regard to "sterilization," first valve 34 is opened to allow the flow of gaseous sterilant from sterilant supply 30 into treatment chamber 22 through first conduit 32. Consequently, the pressure within treatment chamber 22 increases above the pressure within chamber 80.

Gaseous sterilant from sterilant supply 30 is allowed to flow into treatment chamber 22 until the pressure within treatment chamber 22 rises to a second pressure (preferably, about 15 torr, but it is recognized that the pressure of treatment chamber 22 may be allowed to rise to other pressures according to the desired concentration of sterilant within treatment chamber 22).

The resulting differential between the pressure within chamber 80 and the pressure within treatment chamber 22 causes gaseous sterilant to enter lumen device 180 through open end 184 of lumen device 180 and flow through passageway 188 to mating end 182 of lumen device 180. Gaseous sterilant continues to flow through port 162 and along passageway 148 through port 84 of expansion tank 70. It should be understood that residual gas within the at least one lumen device 180 may be "pushed ahead" of the gaseous sterilant as a result of nonturbulent flow or "plug" flow.

Gas entering first end 72 of chamber 80 passes through mixing member 90. In this regard, the gas first contacts vane 100 of mixing member 90 at front edge 104, and then flows through slots 106 defined by vanes 100, before leaving vanes 100 at edge 102. The orientation of vanes 100 causes turbulent flow, thereby mixing gaseous sterilant with residual gas. It is recognized that in the embodiment shown, the mixing is caused by a turbulent flow pattern imparted to gas as it passes through mixing member 90. Gas continues in a turbulent flow pattern as it enters chamber 80. The continued turbulent flow functions to further mix gas entering chamber 80 with any gas (e.g., residual gas) already inside chamber 80. It is appreciated that some degree of mixing of gases inside chamber 80 may also occur as a result of gas diffusion.

After the pressure within treatment chamber 22 and expansion tank 70 reaches a desired level, first valve 34 is then closed to stop the flow of gaseous sterilant from sterilant supply 30 into treatment chamber 22. The pressure within chamber 80 and the pressure within treatment chamber 22 are allowed to equalize. Next, gas is allowed to remain within chamber 80 and within treatment chamber 22 for a desired period to deactivate any contaminates within treatment chamber 22, the lumen device 180 and expansion tank 70.

Following the period that the gas containing gaseous sterilant is allowed to remain in treatment chamber 22 and expansion tank 70, third valve 54 is opened and vacuum source 50 is activated to reduce the pressure within treatment chamber 22. Consequently, gas is removed from treatment chamber 22 and expansion tank 70. In a preferred embodiment, gas is withdrawn from treatment chamber 22 until the pressure within treatment chamber 22 is equal to a third pressure (preferably, about 1 torr). It is recognized that the pressure within treatment chamber 22 may be reduced to any level deemed appropriate by one skilled in the art.

The removal of gas from treatment chamber 22 lowers the pressure within treatment chamber below that of the pressure within chamber 80. The resulting pressure differential causes the gas within chamber 80 to flow from chamber 80 into passageway 148 of conduit 140. As gas exits chamber 80, it again passes through mixing member 90. Gas exiting chamber 80 first contacts vane 100 of mixing member 90 at edge 102 and then flows through the slots 106 defined by vanes 100, before leaving vanes 100 at front edge 104. The orientation of vanes 100 imparts a turbulent flow pattern to the gas as it passes by vanes 100, thereby mixing the contents of the gas. Accordingly, any residual gas that may have remained within chamber 80 is again mixed with gaseous sterilant.

Next, third valve 54 is closed when the pressure within treatment chamber 22 is about 1 torr (it is recognized that pressures other than 1 torr, but less than atmospheric are acceptable). The pressure within treatment chamber 22 is equalized with the pressure within chamber 80. Thereafter, second valve 44 is opened to control the flow of sterile air from air supply 40 into treatment chamber 22. Sterile air flows from treatment chamber 22 into chamber 80 in a manner analogous to that of gaseous sterilant from sterilant supply 30 described above. The pressure within treatment chamber 22 rises to approximately atmospheric pressure.

"Purging" will now be described in detail. The pressure within chamber 80 is allowed to equalize with the pressure within treatment chamber 22. It is recognized that third valve 54 may remain open when second valve 44 is opened. Finally, second valve 44 is closed after sufficient sterile air has been introduced to raise the pressure within treatment chamber 22 to a level equal to atmospheric pressure or some other pressure that is suitable.

It is appreciated that the operations discussed above may occur in the order discussed or in any other suitable sequence that may be recognized by one skilled in the art.

It is recognized that alternates to the preferred embodiment exist. In this regard, that mixing member 90 could be alternately comprised of any device that causes gases contained or flowing within expansion tank assembly 60 to mix. One skilled in the art would recognize a venturi, an orifice, various baffling arrangements, and various expansions and constrictions of conduit or other means to cause mixing of gases flowing into and/or out of expansion tank 80 as providing means to mix gases within expansion tank assembly 60.

For instance, mixing member 90 may be comprised of (a) one or more restrictions dimensioned analogously to venturi nozzles disposed within conduit 140 at either or both ends 142, 144; (b) a venturi nozzle disposed at either or both ports 84, 86 so that all gases entering expansion tank 80 flow turbulently; (c) one or more restrictions or constrictions within passageway 148 dimensioned to cause turbulent flow; or (d) baffles positioned at first end 72 and second end 74 of expansion tank 80.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. An apparatus for the sterilization of a lumen device with a gaseous sterilant, comprising:
   an expansion tank assembly fluidly connectable with at least one lumen device, said expansion tank assembly including an expansion tank;
   a housing defining a sterilization chamber being dimensioned to receive said expansion tank assembly; and
   at least one mixing member disposed within said expansion tank to produce turbulent fluid flow therein, said mixing member comprised of a plurality of vanes.

2. The apparatus for the sterilization of a lumen device of claim 1 wherein said mixing member further comprises:
   a center post and an annular ring, said plurality of vanes extending between said center post and said annular ring.

3. An apparatus for the sterilization of a lumen device with a gaseous sterilant, the apparatus comprising:
   an expansion tank assembly including an expansion tank and a manifold fluidly connected with said expansion tank, wherein said manifold includes:
   a conduit, and
   at least one port for fluidly connecting with a lumen device;
   a housing defining a sterilization chamber being dimensioned to receive said expansion tank assembly; and
   at least one mixing member disposed within said expansion tank assembly to produce turbulent fluid flow therein.

4. The apparatus for the sterilization of a lumen device of claim 3, wherein said at least one mixing member is disposed within said conduit.

5. The apparatus for the sterilization of a lumen device of claim 4, wherein said mixing member is a venturi nozzle.

6. The apparatus for the sterilization of a lumen device of claim 4, wherein said mixing member disposed within said conduit is comprised of a plate disposed across a diameter of said conduit, said plate having an orifice therethrough.

7. An apparatus for the sterilization of a lumen device with a gaseous sterilant, comprising:
   an expansion tank assembly fluidly connectable with at least one lumen device, the expansion tank assembly including:
   an expansion tank; and
   a manifold fluidly connected with the expansion tank, wherein said manifold is comprised of a conduit having a first diameter and a second diameter, said second diameter smaller than said first diameter;
   a housing defining a sterilization chamber being dimensioned to receive said expansion tank assembly; and
   a mixing member to produce turbulent flow within the expansion tank assembly, said mixing member comprised of a portion of said conduit having said second diameter.

8. An apparatus for the sterilization of a lumen device with a gaseous sterilant, comprising:
   an expansion tank assembly fluidly connectable with at least one lumen device, the expansion tank assembly including:
   an expansion tank; and
   a manifold fluidly connected with the expansion tank, wherein said manifold is comprised of a conduit having a first diameter and a second diameter, said second diameter smaller than said first diameter, and
   a housing defining a sterilization chamber being dimensioned to receive said expansion tank assembly; and
   a mixing member to produce turbulent flow within the expansion tank assembly, said mixing member comprised of a portion of said conduit having said first diameter.

9. The apparatus of claim 1, wherein said gaseous sterilant includes at least one chemical selected from the group consisting of the following: vaporized hydrogen peroxide (VHP), ozone, ethylene dioxide, and chlorine dioxide.

10. The apparatus of claim 1, wherein said expansion tank includes a chamber having a volume at least equal to a volume of said lumen device being sterilized.

11. The apparatus of claim 1, wherein said expansion tank includes a chamber, said at least one mixing member located within the chamber.

12. The apparatus of claim 11, wherein said chamber has a first port and a second port, said apparatus having a first mixing member located adjacent to the first port and a second mixing member located adjacent to the second port.

* * * * *